US011774353B2

(12) United States Patent
Major et al.

(10) Patent No.: US 11,774,353 B2
(45) Date of Patent: Oct. 3, 2023

(54) METHODS AND APPARATUSES FOR BIOMIMETIC STANDOFF DETECTION OF HAZARDOUS CHEMICALS

(71) Applicant: The Government of the United States, as represented by the Secretary of the Navy, Washington, DC (US)

(72) Inventors: Kevin Major, Alexandria, VA (US); Kenneth Ewing, Edgewood, MD (US); Jasbinder Sanghera, Ashburn, VA (US); L. Brandon Shaw, Woodbridge, VA (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 471 days.

(21) Appl. No.: 16/669,064

(22) Filed: Oct. 30, 2019

(65) Prior Publication Data
US 2020/0200675 A1    Jun. 25, 2020

Related U.S. Application Data

(60) Provisional application No. 62/752,405, filed on Oct. 30, 2018.

(51) Int. Cl.
*G01N 21/35* (2014.01)
*G01N 33/00* (2006.01)

(52) U.S. Cl.
CPC .......... *G01N 21/35* (2013.01); *G01N 33/0057* (2013.01); *G01N 2201/061* (2013.01)

(58) Field of Classification Search
CPC ............... G01N 21/35; G01N 33/0057; G01N 2201/061
See application file for complete search history.

(56) References Cited

U.S. PATENT DOCUMENTS 7,023,545 B2 * 4/2006 Slater ................. G01J 3/42
356/326
9,625,376 B2 * 4/2017 Elsoee ............... G01N 21/3563
(Continued)

FOREIGN PATENT DOCUMENTS

CA    2945544 C  *  7/2020  ............ G01N 21/35
CA    2858007 C  *  8/2020  ............ G01N 21/314
(Continued)

OTHER PUBLICATIONS

Wojtanowski et al. "Optical stand-off detection of biological and chemical hazards—propects and concerns," IEEE, 2018 Baltic URSI Symposium (Year: 2018).*
(Continued)

*Primary Examiner* — John Fitzgerald
(74) *Attorney, Agent, or Firm* — US Naval Research Laboratory

(57) ABSTRACT

A standoff chemical detection system that includes a source and detector are provided. The source includes: a controller, memory communicatively connected to the controller, optical sources each constructed to operate over different wavelength ranges, and a power supply. The controller controls the plurality of optical sources to emit respective infrared beams towards a target detection area in a sequential order. The detector includes: an image sensor and a controller that is communicatively connected to the image sensor. Memory and the notification device are also communicatively connected to the controller. The image sensor receives attenuated infrared beams emitted by the optical sources sequentially and at least partially attenuated by chemicals in the target detection area. The controller is constructed to calculate stimulus value signals from the recorded image data and determine whether a hazard chemical is located within the
(Continued)

target detection area based on the calculated stimulus value signals.

20 Claims, 11 Drawing Sheets

(56) References Cited

U.S. PATENT DOCUMENTS

| | | | | |
|---|---|---|---|---|
| 9,797,876 B2* | 10/2017 | Islam | | G01N 33/15 |
| 9,857,295 B2 | 1/2018 | Poutous et al. | | |
| 10,598,914 B2* | 3/2020 | Siegel | | G01N 21/6456 |
| 10,794,889 B2* | 10/2020 | Shelton | | G01N 33/22 |
| 11,066,191 B2* | 7/2021 | Salerno, Jr. | | G01N 21/35 |
| 2004/0252300 A1* | 12/2004 | Slater | | G01N 21/35 |
| | | | | 356/318 |
| 2007/0222981 A1* | 9/2007 | Ponsardin | | G01J 3/44 |
| | | | | 356/301 |
| 2014/0218728 A1* | 8/2014 | McLane | | G01J 3/443 |
| | | | | 356/311 |
| 2017/0045442 A1* | 2/2017 | Poutous | | G01N 21/35 |
| 2017/0205290 A1* | 7/2017 | Kester | | G01J 3/0232 |
| 2019/0302012 A1* | 10/2019 | Zheng | | G01N 21/3504 |
| 2022/0026355 A1* | 1/2022 | Normand | | G01N 21/314 |

FOREIGN PATENT DOCUMENTS

| | | | | |
|---|---|---|---|---|
| CA | 2910115 C | * | 8/2020 | ............ G01J 3/0291 |
| CN | 100371821 C | * | 2/2008 | ................ G01J 3/42 |
| GB | 2303447 A | * | 2/1997 | ........... G01N 21/314 |
| JP | 2012513027 A | * | 6/2012 | |
| KR | 20170049640 A | | 5/2017 | |
| WO | WO-2018213212 A1 | * | 11/2018 | ............ G01J 3/0275 |
| WO | WO-2019157250 A9 | * | 10/2019 | ........... A61B 5/0086 |

OTHER PUBLICATIONS

Moore, D.S.; Review of Scientific Instruments, 2004, 75, 2499-2512.
Cotte-Rodriguez, I.; Cooks, R.G.; Chemical Communications, 2006, 28, 2968-2970.
Singh, S.; Journal of Hazardous Materials, 2007, 144, 15-28.
Sanders, N.L.; Kothari, S.; Huang, G.; Salazar, G.; Cooks, R.G.; Analytical Chemistry, 2010, 82(12), 5313-5316.
Lin, H.; Suslick, K.S.; Journal of the American Chemical Society, 2010, 132(44), 15519-15521.
Hendricks, P.I.; Dalgleish, J.K.; Shelley, J.T.; Kirleis, M.A.; McNicholas, M.T.; Li, L.; Chen, T.; Chen, C.; Duncan, J.S.; Boudreau, F.; Noll, R.J.; Denton, J.P.; Roach, T.A.; Ouyang, Z.; Cooks, R.G.; Analytical Chemistry, 2014, 86(6), 2900-2908.
Junju, F.P.M.; Maher, S.; Li, A; Syed, S.U.; Smith, B.; Heeren, R.M.A.; Taylor, S.; Cooks, R.G.; Analytical Chemistry, 2015, 10047-10055.
Brown, K.E.; Greenfield, M.T.; McGrane, S.D.; Moore, D.S.; Analytical and Bioanalytical Chemistry, 2016, 408, 35-47.
Liu, X.; Van Neste, C. W.; Gupta, M.; Tsui, Y. Y.; Kim, S.; Thundat, T. Sens. Actuators, B 2014, 191, 450-456.
Sharma, R. C.; Kumar, D.; Bhardwaj, N.; Gupta, S.; Chandra, H.; Maini, AK. Opt. Comm. 2013, 309, 44-49.
Van Neste, C. W.; Senesac, L. R.; Thundat, T. Anal. Chem. 2009, 81, 1952-1956.
Tuschel, D. D.; Mikhonin, AV.; Lemoff, B. E.; Asher, S. A Appl. Spectrosc. 2010, 64, 425-432.
Pettersson, A; Johansson, I.; Wallin, S.; Nordberg, M.; Ostmark, H. Propell. Explos. Pyrot. 2009, 34, 297-306.
Department of Homeland Security, System Assesment and Validation for Emergency Responders (SAVER) program: "Passive Infrared Systems for Remote Chemical Detection Assessment Report," Sep. 2016.
Poutous, M.; Major, K.J.; Ewing, K.J.; Sanghera, J.; Aggarwal, I.; Applied Spectroscopy, 2015, 69(3), 305-313.
Major, K.J.; Poutous, M.K.; Dunnill, K.F.; Deguzman, P.C.; Sanghera, J.S.; Aggarwal, I.D.; Ewing, K.J.; Analytical Chemistry, 2016, 88(23), 11491-11947.
Major, K.J.; Ewing, K.J.; Poutous, M.K.; Sanghera, J.S.; Aggarwal, I.D.; In Detection and Sensing of Mines, Explosives Objects, and Obscured Targets XIX, Proceedings of SPIE, 2014, 9072.
Major, K.J.; Poutous, M.K.; Dunnill, K.F.; Ewing, K.J.; Sanghera, J.S.; Aggarwal, I.D.; In Next Generation Spectroscopic Technologies VII, Proceedings of SPIE, 2015, 9482.
Major, K.J.; Poutous, M.K.; Dunnill, K.F.; Ewing, K.J.; Sanghera, J.S.; Deguzman, P.C.; Aggarwal, I.D.; InDetectionandSensingofMines, Explosive Objects, and Obscured Targets XXI, Proceedings of SPIE, 2016, 9823.
Major, K.J.; Poutous, M.K.; Ewing, K.J.; Dunnill, K.F.; Sanghera, J.S.; Aggarwal, I.D.; Analytical Chemistry, 2015, 87(17), 8798-8808.

* cited by examiner

METHODS AND APPARATUSES FOR BIOMIMETIC STANDOFF DETECTION OF HAZARDOUS CHEMICALS

BACKGROUND

Field of the Invention

The present application relates generally to biomimetic standoff detection of hazardous chemicals.

Description of Related Art

Since World War I, chemical warfare agents have become an ever present concern for military operations. The existence and stockpiling of chemical warfare agents (CWAs) by different countries throughout the world presents a clear and present danger to the military and civilians. This threat is magnified by the uptick in terrorism in the early part of the $21^{st}$ century. Both civilians and military forces are now face the threat of an invisible (to the naked eye) weapon being deployed against them with little notice and potentially catastrophic consequences. Detection of chemical warfare agents represents a significant need for both the military as well as civilian communities.

For a chemical agent detection system to provide robust protection, it is necessary for that system to: (i) detect the chemical agent at a distance so as to allow adequate time to warn at risk individuals, and (ii) detect the presence of the chemical warfare agent before the agent reaches hazardous concentrations. Meeting these requirements is complicated by the presence of other non-toxic chemicals in the atmosphere that could be incorrectly identified as the CWA/toxic chemical. Background chemicals, such as gasoline vapor or diesel engine exhaust present in the monitored environment require that any detection system is capable of discriminating between CWAs and other chemicals that present an immediate hazard and non-weaponized background chemicals in order to eliminate false alarms.

Existing standoff detection systems include single filter systems, multi-band imagers, and hyperspectral systems. Single filter systems include a single filter that responds to a single absorption band of the target chemical. FIG. 1 is illustrative. In FIG. 1 an optical source 102 emits electromagnetic radiation 104A over a broad wavelength/frequency in the direction of a detection area 1000. Some of that electromagnetic radiation is preferentially absorbed by the target agent contained within the detection area 1000. The radiation 104B emanating from the detection area 1000 will therefore have decreased amplitude over the wavelength/frequency range corresponding to the target agent. An optical filter 106 designed to allow transmission of the particular wavelength/frequency range corresponding to the target agent while blocking others. If the target agent is present in the detection area 100, then radiation 104B within the wavelength/frequency range corresponding to the target agent passes through filter 106 and is incident on an optical sensor 108. Sensor 108 converts the incident radiation 104B into a digital signal which is analyzed by a processor 110. If the target agent is not present in the detection area 1000, then no decrease in amplitude is expected. If, however, the target agent is present then a decrease in amplitude is expected. Thus, the measured amplitude of sensor 108 can be used to determine the presence of a target agent in the detection area 1000.

While these single filter systems offer advantages due to their simplicity, the use of only a single filter means the system exhibits extremely poor selectivity and cannot be used for discrimination of a target agent against a complex background where non-hazardous chemical agents may absorb radiation of the same wavelength/frequency as the hazardous chemical. Multi-band and hyperspectral systems offer better performance compared to a single filter system, but are much more expensive and fragile, making them unsuitable for use in a field environment. Therefore, it would be desirable to have a chemical detection system that could mitigate the deficiencies of the existing systems.

SUMMARY OF THE INVENTION

One or more of the above limitations may be diminished by structures and methods described herein.

In one embodiment, a system for standoff chemical detection is provided. The system includes a source and a detector. The source includes: a source controller, memory communicatively connected to the source controller, a plurality of optical sources each constructed to operate over different wavelength ranges, and configured to receive instructions from the source controller, and a power supply. The source controller is configured to control the plurality of optical sources to emit respective infrared beams towards a target detection area in a sequential order. The detector includes an image sensor, a detector controller communicatively connected to the image sensor, memory communicatively connected to the detector controller, and a notification device communicatively connected to the detection controller. The image sensor is constructed to receive attenuated infrared beams emitted by the plurality of optical sources sequentially and at least partially attenuated by one or more chemicals in a target detection area. The image sensor is constructed to generate digital data based on the received attenuated infrared beams. The detector controller is constructed to calculate stimulus value signals from the recorded image data and determine whether a hazard chemical is located within the target detection area based on the calculated stimulus value signals.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

Figure 1:
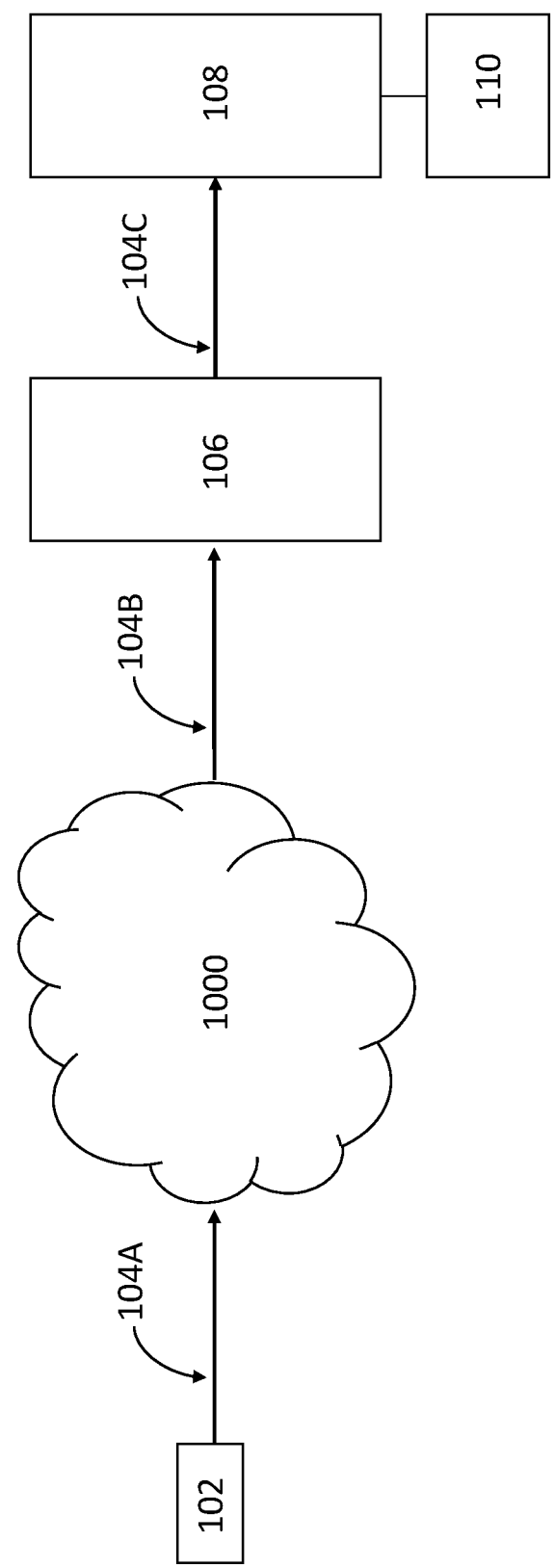
FIG. 1 is a schematic illustration of existing filter based standoff detection systems.

Different ones of the Figures may have at least some reference numerals that are the same in order to identify the same components, although a detailed description of each such component may not be provided below with respect to each Figure.

DETAILED DESCRIPTION OF THE PREFERRED EMBODIMENTS

In accordance with example aspects described herein are method and apparatuses for biomimetic standoff detection.

Figure 2A:
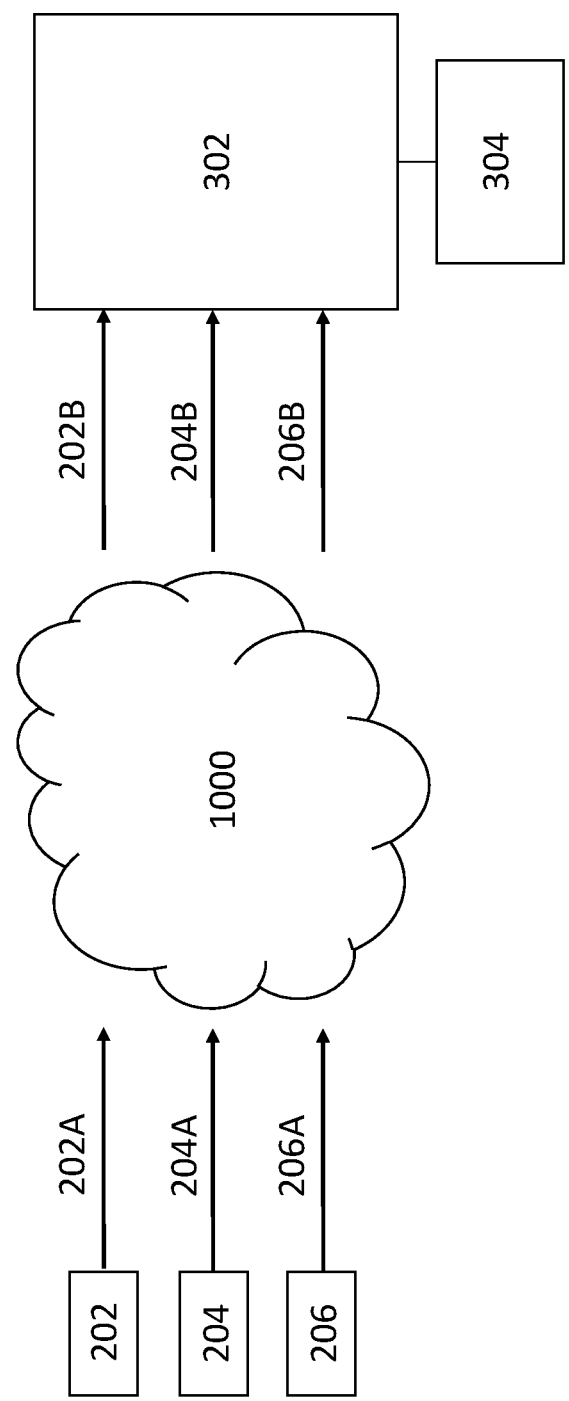
FIG. 2A is a schematic illustration of some principals implemented in the embodiments described herein.
Figure 2B:
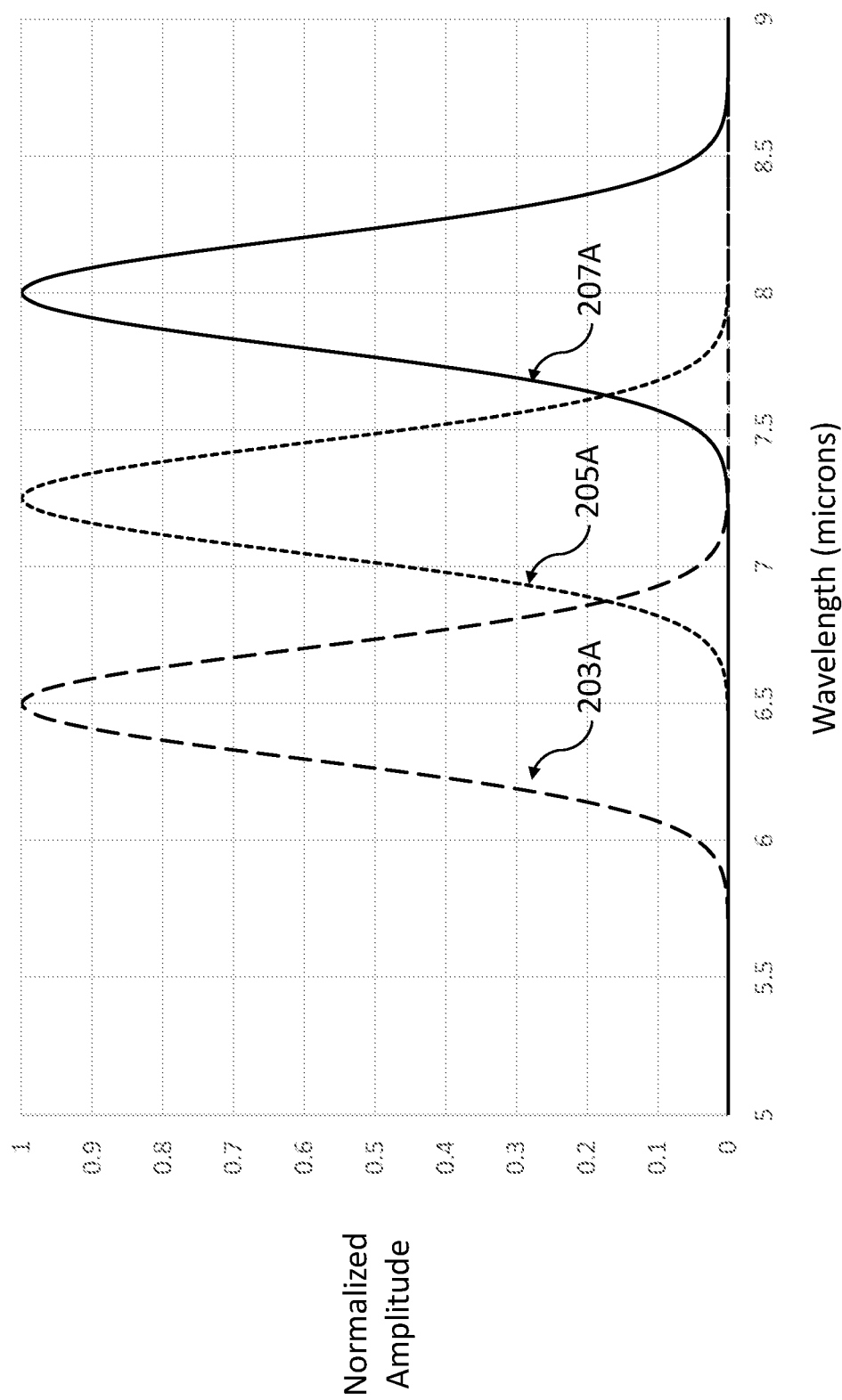
FIG. 2B is a plot of normalized amplitude versus wavelength for three optical sources.

FIGS. 2A-D illustrate the principals behind the operation of biomimetic standoff detection systems described herein. As shown in FIG. 2A, a plurality of optical sources 202, 204, and 206 are provided and constructed to emit infrared radiation in the form of beams 202A, 204A, and 206A towards a target detection area 1000. Optical sources 202, 204, and 206 may preferably be light emitting diodes (LEDs), quantum cascade lasers (QCLs), interband cascade lasers (ICLs), quantum dot emitters, or fluorescence emitters. As shown in FIG. 2A, the optical sources 202, 204, and 206 are selected such that each selected optical source has some spectral overlap with at least one other selected optical source. Within the target detection area 1000 are one or more chemicals. The chemicals within the target detection area 1000 may include a hazardous weaponized chemical (e.g., a chemical warfare agent such as VX), along with other non-weaponized chemicals (e.g., acetone). The infrared radiation emitted by the optical sources 202A, 204A, and 206A, in a preferred embodiment, is within the mid-wave infrared region (MWIR), which is 2-8 µm, or the long wavelength infrared region (LWIR), which is 8-15 µm. Beams 202A, 204A, and 206A may have Gaussian or pseudo Gaussian profiles that partially overlap. FIG. 2B is illustrative.

Figure 2C:
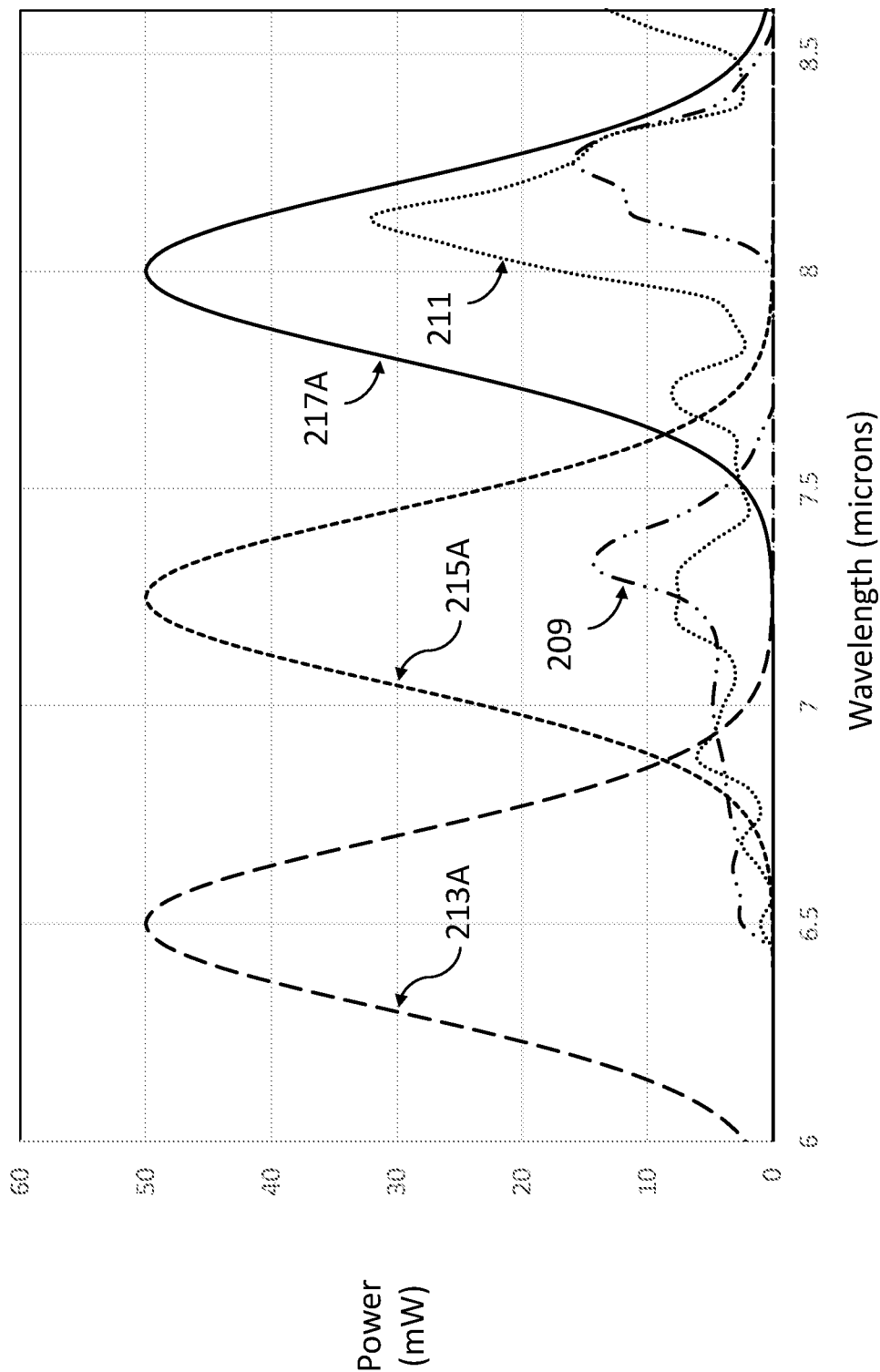
FIG. 2C is a plot of amplitude versus wavelength for the three optical sources along with absorbance spectra for acetone vapor and the chemical warfare agent VX vapor.

FIG. 2B shows three normalized amplitude profiles 203A, 205A, and 207A respectively corresponding to beams 202A, 204A, and 206A. Profiles 203A, 205A, and 207A have mean spectral responses (or center wavelengths) of 6.5 µm, 7.25 µm, and 8.0 µm, respectively. The standard deviation (or bandwidth) for each of these profiles is 0.2 µm. Of course, these values are dependent on the type of optical sources used. Some optical sources may have different means and standard deviations or produce pseudo-Gaussian profiles. In the exemplary embodiment shown in FIG. 2B, profiles 203A, 205A, and 207A are within the mid-wave infrared region, however the selection of these particular profiles and infrared wavelengths is merely exemplary. By changing the emitting properties of sources 202, 204, and 206, the profiles 203A, 205A, and 207A may shifted within the MWIR and LWIR regions. In a preferred embodiment, the optical sources 202, 204, and 206 (and their corresponding profiles 203A, 205A, and 207A) emit infrared radiation that is responsive to known hazardous chemicals. FIG. 2C is illustrative.

FIG. 2C shows amplitude profiles 213A, 215A, and 217A that are substantially similar to profiles 203A, 205A, and 207A except they are not normalized but rather show a maximum power of 50 mW at their wavelength of maximum emission. Also shown are absorbance spectra for acetone (profile 209) and VX (profiles 211). When infrared radiation passes through a gas containing a chemical that is responsive to one or more frequencies of that infrared radiation, some of the energy from the infrared radiation is absorbed by the chemical. If one is measuring the amplitude of the infrared radiation, after passing through the gas, as a function of frequency, there will be a drop in amplitude over the frequencies that the chemical is responsive to. That plot when presented as a ratio out of 100, where 100 is the amplitude of the infrared radiation with no chemical present is called a transmission spectrum, in units of percentage (% T). One may then calculate an absorbance spectrum by subtracting the common logarithm of this spectrum at each wavenumber from 2. For such an absorbance spectrum, the peaks indicate the frequencies over which the chemical is responsive to the infrared radiation. Producing such spectra requires a spectrometer which is a very delicate piece of equipment that is not suitable for field use. However, one can detect the presence of a chemical within the gas without such equipment using a biomimetic approach.

As indicated above, FIG. 2C shows acetone's absorbance spectrum 209 and VX's absorbance spectrum 211 from 6.0-8.6 µm, along with profiles 213A, 215A, and 217A corresponding to one embodiment of optical sources 202, 204, and 206. It is clear from FIG. 2C, that radiation emitted from each optical source will interact differently with acetone and VX. For instance, the absorbance amplitudes for both acetone and VX are relatively low over the range of profile 213A (approximately 6-7 µm) corresponding to source 202. In fact, between 6-6.5 µm acetone and VX hardly absorb any radiation. However, the absorbance amplitudes for both acetone and VX increase over a range of 6.75-7.75 µm, which substantially corresponds to profile 215A. Thus, radiation emitted from optical source 204 (corresponding to profile 215A) will be absorbed by both acetone and VX more than radiation emitted from optical source 202. Importantly though, acetone and VX do not show identical responsiveness to source 204. For instance, in a range of 7.25-7.5 µm acetone shows nearly double the absorption of VX. As discussed below, these differences in absorption will be important when it comes to discriminating between different chemicals. Finally, for completeness, the absorbance amplitudes for VX are much higher than acetone in the range of 7.5-8.5 µm, which substantially corresponds to profile 217A. As such, it is expected that VX will absorb more radiation from source 206 (corresponding to profile 217A) than acetone.

Figure 2D:
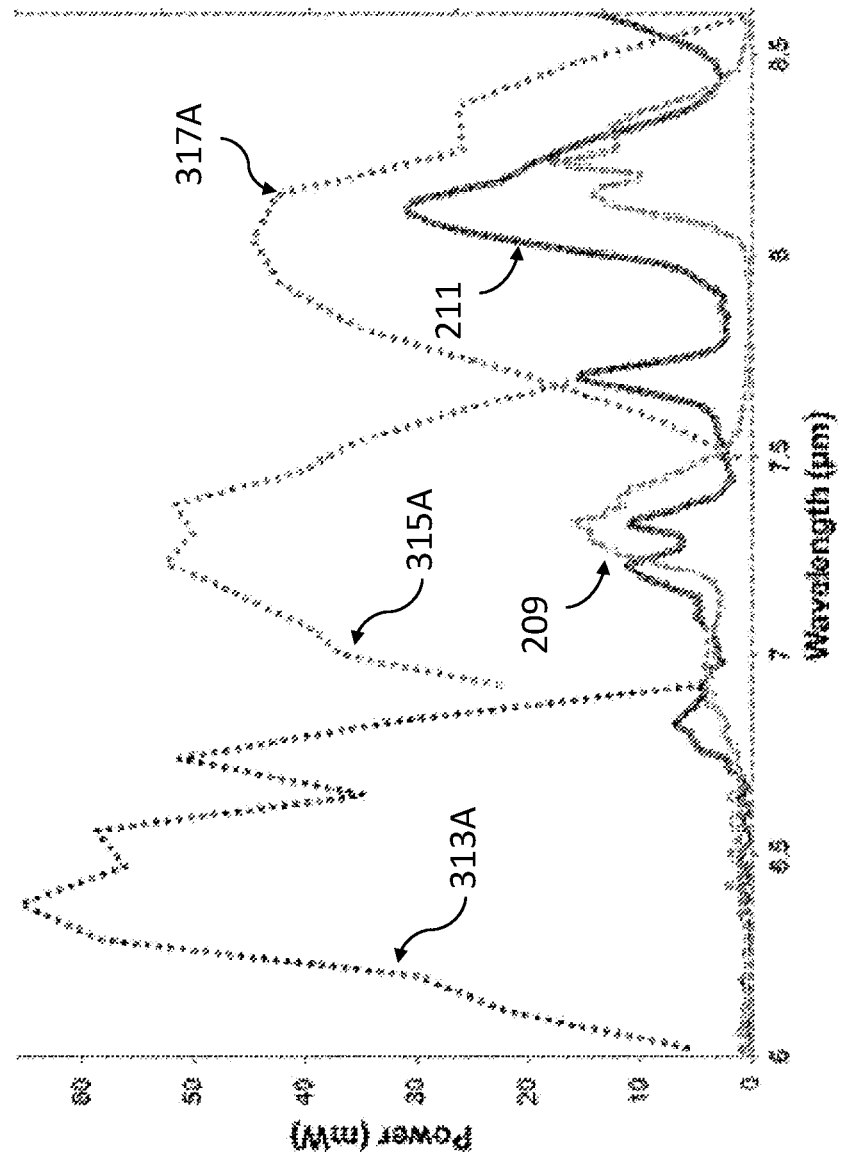
FIG. 2D is another plot of amplitude versus wavelength when pseudo-Gaussian profiles are used.

In FIG. 2C, the optical sources 202, 204, and 206, produce Gaussian profiles. However, pseudo-Gaussian profiles may also be generated by optical sources 202, 204, and 206, as shown in FIG. 2D. FIG. 2D shows amplitude profiles 313A, 315A, and 317A in an embodiment where sources 202, 204, and 206 are quantum cascade lasers. It is self-evident from FIG. 2D that profiles 313A, 315A, and 317A are not Gaussian profiles, but rather pseudo-Gaussian profiles where the intensity of radiation is approximately evenly distributed around a mean and the majority of the radiation lies within one standard deviation of the mean, falling off thereafter. In contrast to FIG. 2C, the mean amplitudes of sources 202, 204, and 206 in FIG. 2D are not equal.

Having described the general approach to chemical detection, systems for implementing the same will now be described.

Figure 3:
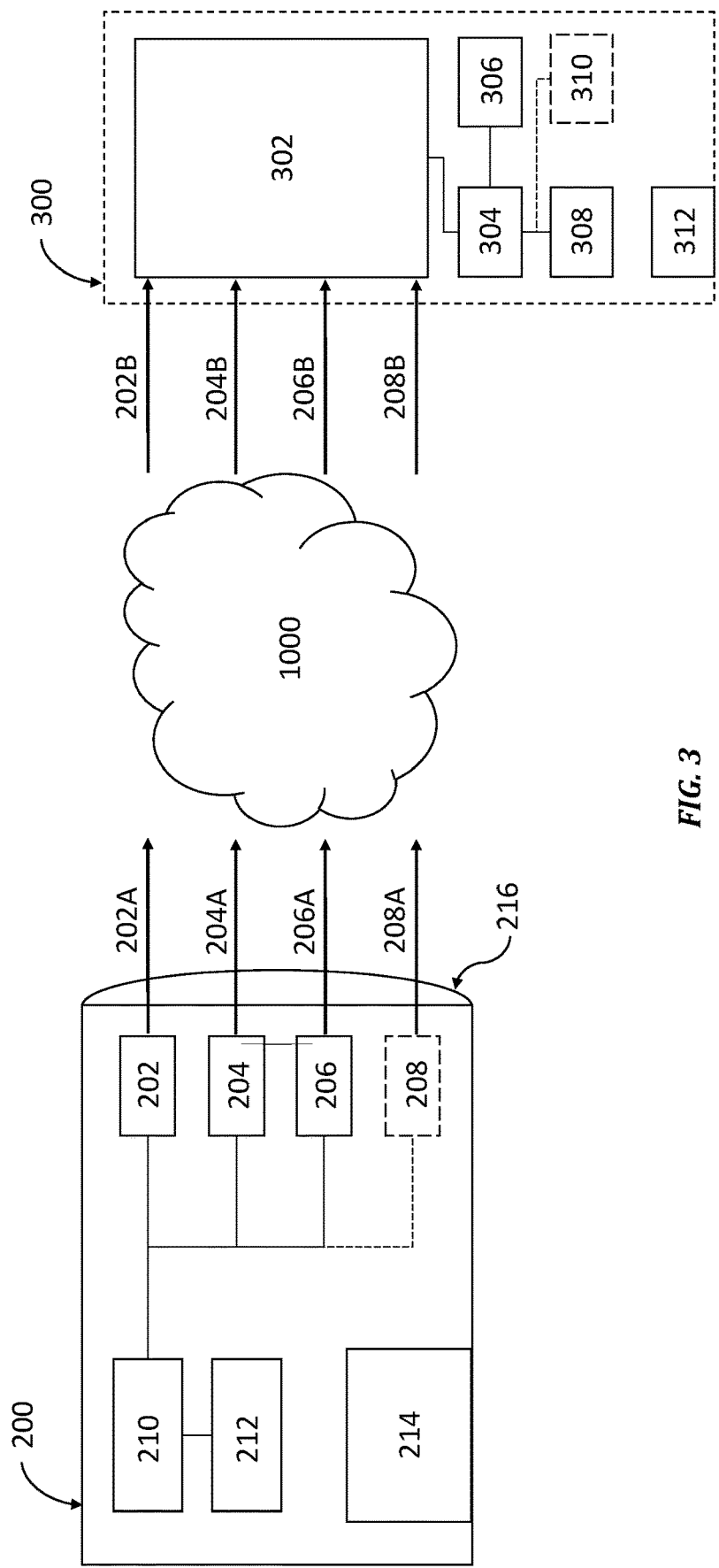
FIG. 3 is a schematic illustration of standoff chemical detection system according to one embodiment.

FIG. 3 is a schematic illustration of a system for standoff chemical detection. A source 200 is provided and includes a controller 210, memory 212, optical sources 202, 204, and 206, and a power supply 214. Power supply 214 may be an internal power supply (e.g., a battery), a connection for receiving external power, or a self-generating source of power such as a photovoltaic device. Power supply 214 supplies power to the controller 210, memory 212, and the optical sources 202, 204, and 206. In one embodiment, an additional optical source 208 may be provided and used as a reference source. The reference source 208 is selected such that it does not have spectral overlap with the absorption bands of the chemicals of interest to be detected. Therefore, the power received back from this source should be stable whether a chemical of interest is present between the sources and the detector. In this fashion, any optical loss (i.e. scattering, etc.) not attributable to chemical absorption may be accounted for, as well as accounting for any variations in the stability of the detector over time due to heating or other phenomenon. If optical source 208 is provided, then it is controlled by controller 210 in the same manner as optical sources 202, 204, and 206, as described below.

Controller 210 includes a processor which may be a central processing unit (CPU), microprocessor, or a microcontroller. Controller 210 is communicatively coupled to memory 212 which stores a control program that, when executed, causes the controller 210 to turn on and off the optical sources 202, 204, and 206 (and 208 if applicable) in sequential order, as discussed below. By controlling the optical sources 202, 204, and 206 (and 208 if applicable) such that only one of the sources is active at a time (in a preferred embodiment) the processing requirements on the sensor system 300 are reduced. The optical sources 202, 204, and 206 emit beams of radiation, 202A, 204A, and 206A. If provided, source 208 emits a beam of radiation 208A. As discussed above, the radiation preferably falls within the MWIR and LWIR, that is 2-15 μm, and the beams exhibit Gaussian or pseudo-Gaussian profiles about their respective maximum emission values. Except, as discussed above, beam 208A has a profile that is not responsive to a target of interest. The beams of radiation 202A, 204A, and 206A (and possibly 208A) are directed through an optical element 216 that focuses the beams of radiation and directs them toward a target detection 1000. The optical element may be a lens or a plurality lens that are arranged such that beams 202A, 204A, 206A and 208A (if applicable) are collimated.

Beams 202A, 204A, and 206A (and possibly 208A) are directed to a target detection area 1000 in which one or more chemical agents are located. As discussed above, if a chemical located within the target detection area is responsive to the wavelengths of radiation emitted by the optical sources 202, 204, and 206, then the chemical will absorb a portion of that radiation resulting in attenuated beams 202B, 204B, and 206B. Beams 208B by design should not be attenuated by targets of interest. Beams 202B, 204B, 206B, and 208B (if applicable) are then incident on a detector 300.

Detector 300 includes an image sensor 302 which is communicatively coupled to a controller 304. Image sensor 302 may be an infrared photodiode optical sensor, a PbSe image sensor, a Si microbolometer, a $VO_x$ microbolometer, an infrared focal plane array, an HgCdTe detector, a deuterated triglycine sulfate detector, or other infrared pyroelectric, thermoelectric, or semiconductor detector. Image sensor 302 may be formed by a single-pixel "point" sensor as well as an n×m pixel array (see FIG. 8A). A single-pixel point sensor may be consider an n×m array where both n and m are equal to 1. In the case of a multi-pixel array n>1 and/or m>1. Controller 304 includes a processor which may be a central processing unit (CPU), microprocessor, or a microcontroller. Controller 304 provides for overall control of the detector 300 and is communicatively coupled to memory 306 which stores a control program that, when executed, causes the controller 304 to receive and process data from the image sensor 302. Memory 306 also includes storage space that may be used for storage of data received from the image sensor 302 and storage of the data processing results. Controller 304 is also coupled to a notification device 308. Notification device 308 may be an electronic device that displays the results of processes performed by controller 304 and/or provides audio alerts or information. For example, if controller 304 determines that a hazardous chemical exists within the target area 1000, then notification device 308 may display the name of the detected chemical threat and provide an audio indication in the form of an alarm. In another embodiment, an I/O connection 310 may be provided so as to allow for communication between the detector 300 and another device. The I/O connection 310 may be a wired connection or a wireless connection (e.g., Wi-Fi, Bluetooth, NFC, or satellite). Finally, detector 300 includes a power supply 312 which may be an internal power supply (e.g., a battery), a connection for receiving external power, or a self-generating source of power such as a photovoltaic device. Power supply 312 supplies power to the image sensor 302, controller 304, memory 306, the notification device 308, and the I/O connection 310 (if applicable).

Figures 8A, 8B:
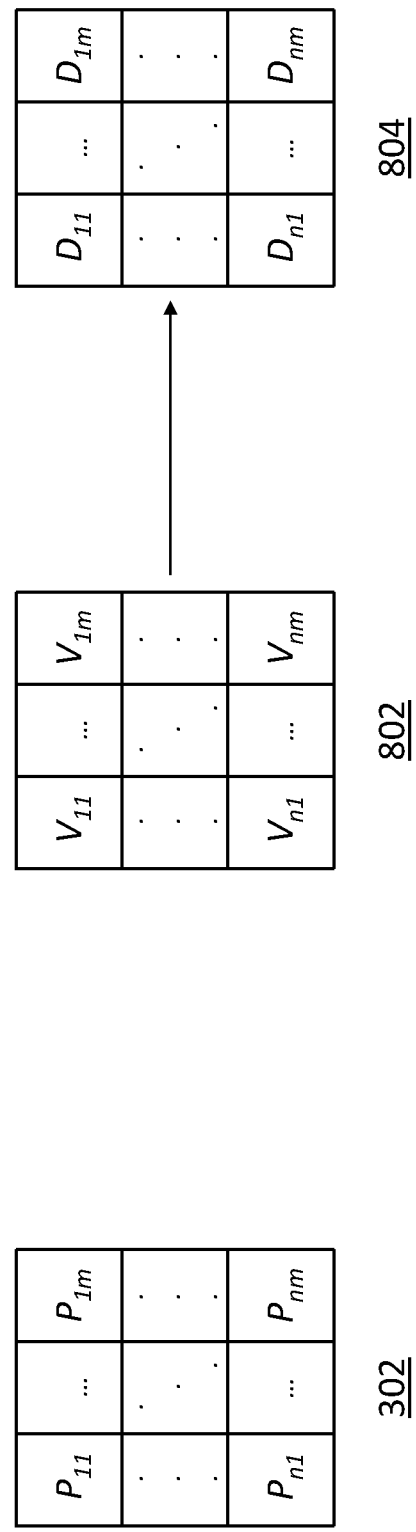
FIG. 8A is a schematic illustration of an n×m pixel array.
FIG. 8B is a schematic illustration of the conversion of voltages corresponding to pixels in a pixel array to digital image data.

Having described the structure of detector 300, the process by which detector 300 analyzes received radiation will now be discussed. As discussed above, in a preferred embodiment, the optical sources 202, 204, and 206 (and possibly 208) are controlled such that only one of the optical sources emits a beam of radiation at a time. As a result, attenuated radiation beams 202B, 204B, and 206B (and possibly 208B) are incident on the image sensor 302 one at a time. The degree to one of the beams 202B, 204B, and 206B is attenuated depends upon the responsiveness of the chemicals within the target detection area 1000 to that those wavelengths. Consequently, the amplitude of infrared radiation recorded by the image sensor 302 is dependent upon the degree of beam attenuation by the chemicals present in the target detection area 1000. The infrared radiation incident on sensor 302 produces voltages for each pixel of sensor 302 corresponding to the amplitude of the received radiation. After a prescribed time, those voltages are readout and converted into digital data which is then provided to controller 304. FIG. 8B illustrates the conversion of voltages 802, corresponding to the pixels in sensor 302, into digital image data 804. After receiving data from sensor 302 corresponding to each of beams 202, 204, and 206, controller 304 may use stimulus value signals to determine the chemical present in the target detection area. The stimulus value signals are physically defined by the integrated response between a molecular vibrational signature of a chemical and the spectral response of each Gaussian or pseudo-Gaussian source. In the case of a photosensor, the voltage(s) produced by the sensor are the integrated response between the molecular vibrational signature of a chemical and the spectral response of each Gaussian or pseudo-Gaussian source. Depending on the analysis technique, controller 304 may use the recorded voltages as the stimulus value signals or the difference(s) between the recorded voltage(s) and reference voltage(s) (recorded when no chemical is present in the target detection area) as the stimulus value signals. The difference(s) may be used by controller 304 as stimulus value signal(s) in a comparative discrimination spectral detection (CDSD) technique to determine the chemicals present in the target detection, as described in U.S. Pat. No. 9,857,295, the contents of which are incorporated by reference herein in their entirety. In another embodiment, controller 304 may analyze the stimulus value signals using CIE-IR (Commission on Illumination Infrared Analysis) to determine the chemicals present in the target detection area 1000, as described in U.S. patent application Ser. No. 16/571,461 the contents of which are incorporated by reference herein in their entirety. In the case of CIE-IR, the voltages recorded by the sensor 302 are the stimulus value signals. Conversely, controller 304 may analyze the stimulus value signals by other commonly employed data classification methods including but not limited to linear discriminate analysis or support vector machines.

Figure 4:
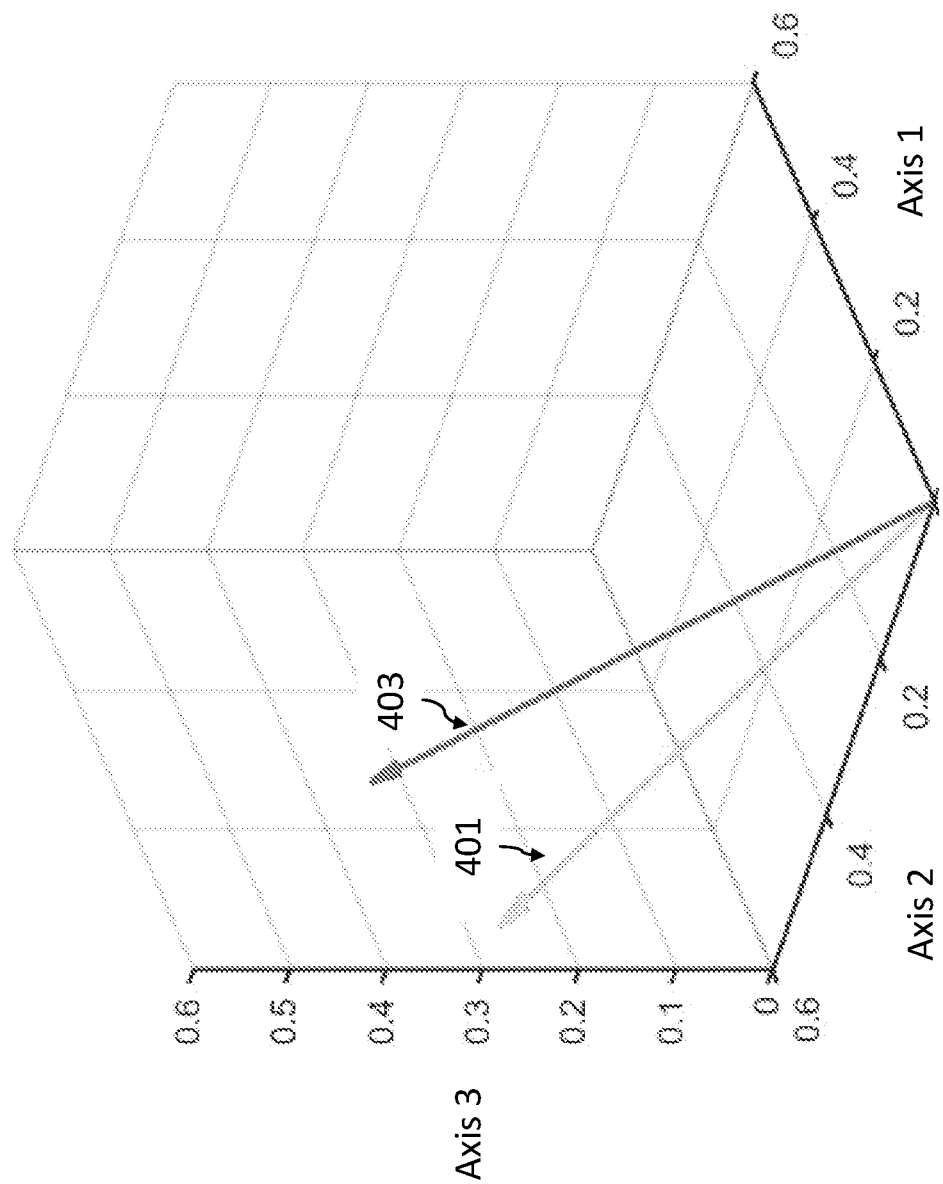
FIG. 4 is a three-dimensional plot of two vectors corresponding to acetone and VX, respectively.

FIG. 4 illustrates two vectors 401 and 403 in three-dimensional space formed from the stimulus value signals calculated by controller 304. Vector 401 corresponds to acetone. Vector 403 corresponds to VX. It is self-evident from FIG. 4, that vectors 401 and 403 point in different directions. Memory 306 may contain a plurality of vectors formed from stimulus value signals with each vector corresponding to a different chemical. Controller 304, in one embodiment, may compare a vector calculated based on stimulus value signals from images recorded by sensor 302 to the plurality of vectors stored in memory 306. If the difference between a calculated vector and a stored vector is negligible, then controller 306 may deem the chemical corresponding to the stored vector to be present in the target detection area 1000. If the chemical corresponding to the stored vector is a hazardous or threat chemical, then controller 304 may cause notification device 308 to display the name of the identified chemical and/or provide an audible alarm. Controller 304 may also control I/O connection 310 to transmit the identifying information on the chemical (e.g., the detected chemical's name) to another device.

Figure 5:
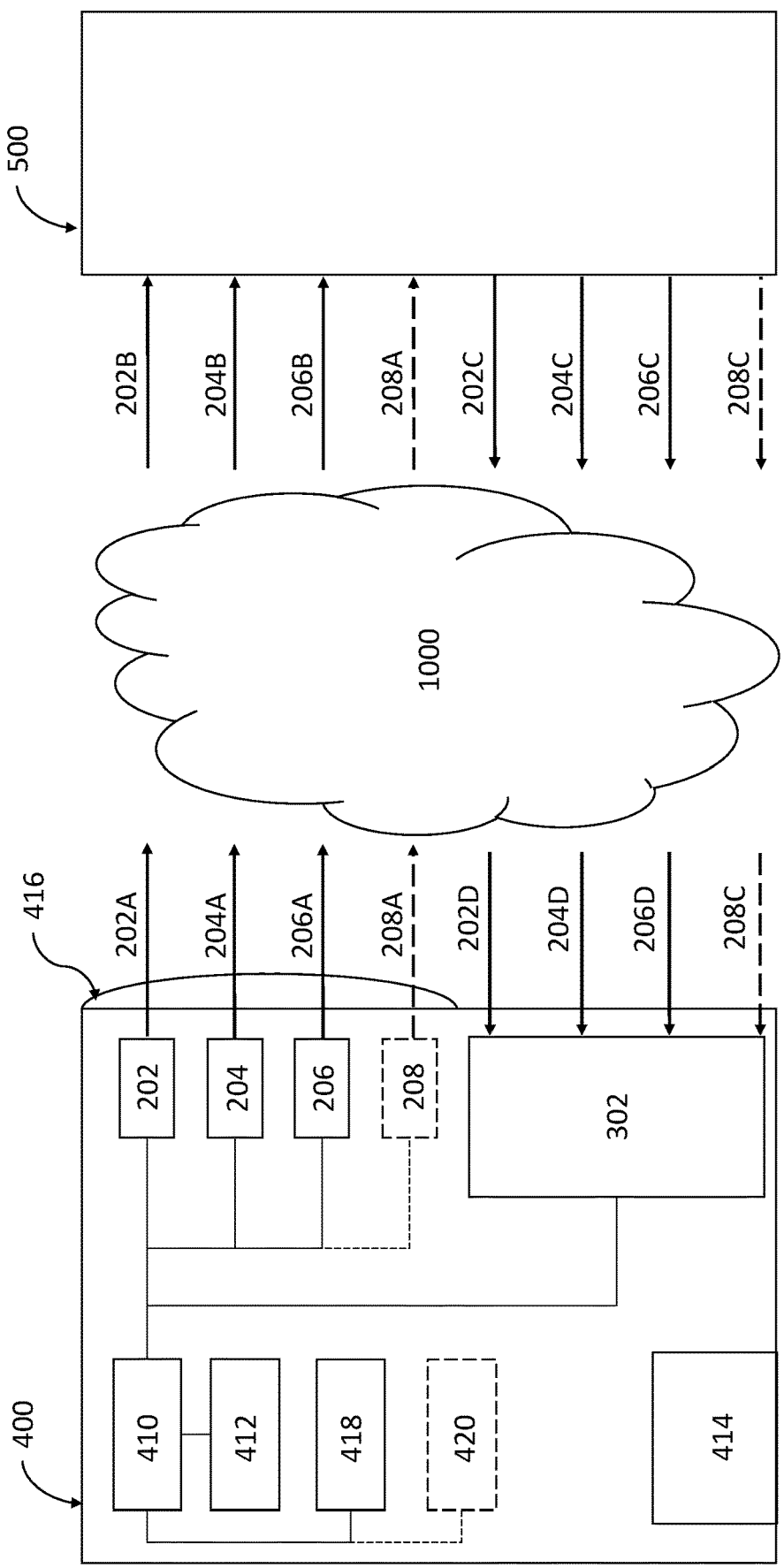
FIG. 5 is a schematic illustration of a standoff chemical detection system according to another embodiment.

FIG. 5 illustrates another system for standoff chemical detection. Unlike the system shown in FIG. 3, the optical sources and the sensor are not separated but rather combined into a single source-detector 400. Source-detector 400 includes a controller 410, memory 412, an optical element 416, a notification device 418, an optional I/O connection 420, optical sources 202, 204, and 206 (and 208 in one embodiment), optical sensor 302, and a power supply 414.

Controller 410 includes a processor which may be a central processing unit (CPU), microprocessor, or a microcontroller. Controller 410 provides overall control of the detector 400, and is communicatively coupled to memory 412 which stores a control program that, when executed, causes the controller 410 to receive and process data from the image sensor 302. Memory 412 also includes storage space that may be used for storage of data received from the image sensor 302 and storage of the data processing results. Controller 410 is also coupled to a notification device 418. Notification device 418 may be an electronic device that displays the results of processes performed by controller 410 and/or provides audio alerts or information. For example, if controller 410 determines that a hazardous chemical exists within the target detection area 1000, then notification device 418 may display the name of the detected chemical threat and provide an audio indication in the form of an alarm. In one embodiment, an I/O connection 420 is provided that allows for communication between the detector 400 and another device. The I/O connection 420 may be a wired connection or a wireless connection (e.g., Wi-Fi, Bluetooth, NFC, or satellite). Power supply 414 may be an internal power supply (e.g., a battery), a connection for receiving external power, or a self-generating source of power such as a photovoltaic device. Power supply 414 supplies power to all of the components of detector 400.

Having described the structure of source-detector 400, attention will now be directed to its operation. Controller 410 controls the optical sources 202, 204, and 206 (and optionally 208) to emit infrared radiation in the form of beams 202A, 204A, and 206A (and possibly 208A). In a preferred embodiment, the optical sources 202, 204, and 206 (and possibly 208) are turned on and off in a sequential manner such that only one optical source is active at a time. Optical sources 202, 204, 206, and 208 are the same as those discussed above, as such a detailed description of those sources is omitted for brevity.

Beams 202A, 204A, and 206A (and possibly 208A) are directed towards a target detection area 1000 sequentially under the control of controller 410. As discussed above, beams 202A, 204A, and 206A are attenuated by one or more chemicals located within the target detection area 1000 forming attenuated beams 202B, 204B, and 206B. Beam 208A is not attenuated by a target chemical. The attenuated beams 202B, 204B, and 206B (and possibly 208A) are then provided to a retroreflector 500 which reflects them back towards detector 400 thereby forming reflected beams 202C, 204C, and 206C (and possibly 208C). The reflected beams 202C, 204C, and 206C may pass through the target detection area 1000 again where they are further attenuated by one or more chemicals present in the target detection area 1000 forming attenuated reflected beams 202D, 204D, and 206D. The attenuated reflected beams 202D, 204D, and 206D (and possibly 208C) are provided, sequentially, to an image sensor 302. As discussed above, image sensor 302 converts the incident radiation into digital data which is provided to controller 410. Controller 410 uses the voltages or the differences in voltages from sensor 302 (as explained above). Using one of the analysis techniques discussed above, controller 410 determines which chemical is present in the target detection area 1000. If a hazardous chemical is detected, controller 410 causes the notification device 418 to provide a visual/audio warning that indicates the presence of a hazardous chemical. Controller 410 may also cause I/O connection 420 to send a signal to another device indicating the presence of a hazardous chemical within the target detection area 1000.

Having described the structure and operation of two detection systems, shown in FIGS. 3 and 5, attention will now be directed to implementations of those systems.

Figure 6:
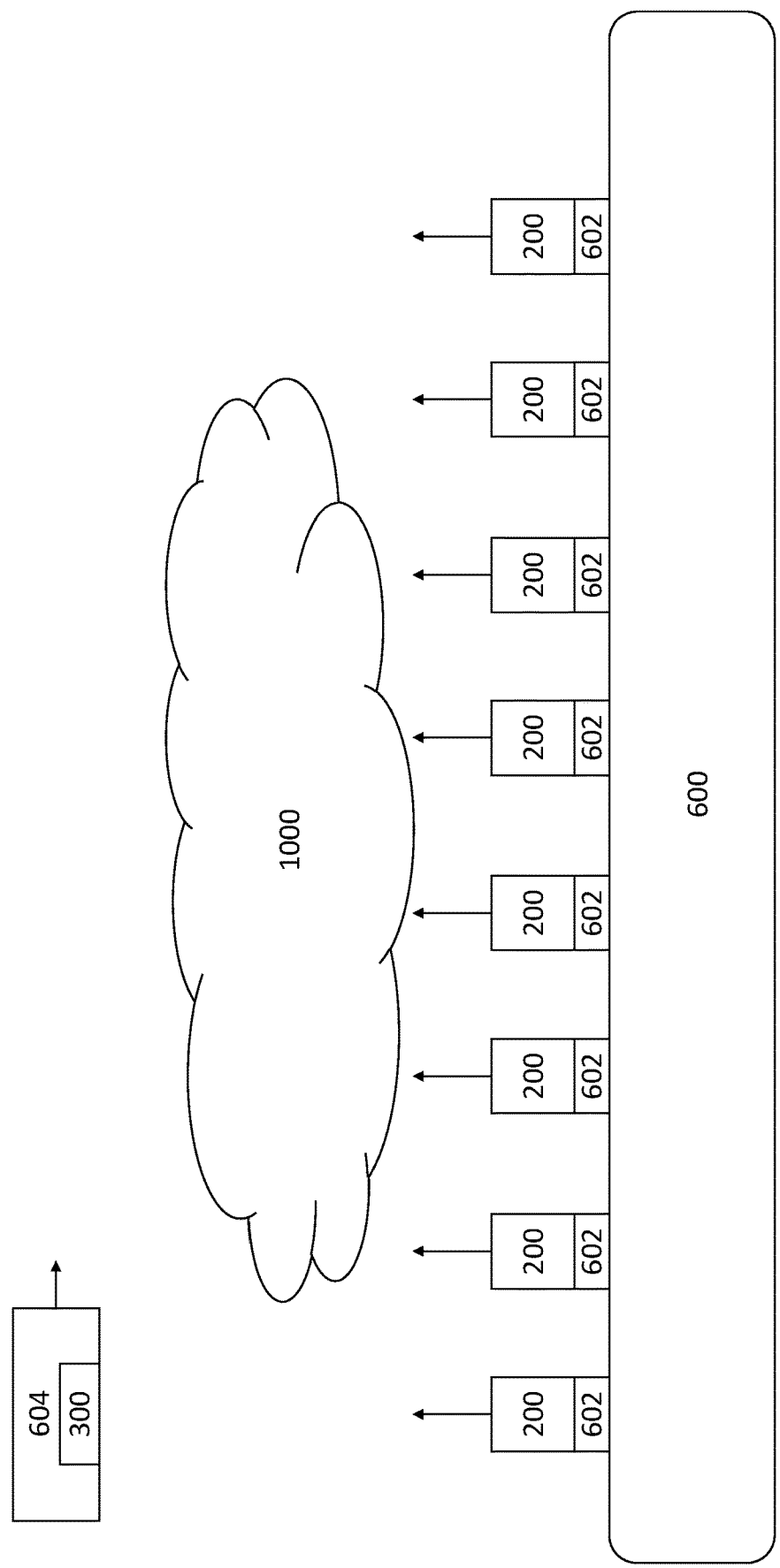
FIG. 6 is an illustration showing the deployment of sources in a field and the process by which data is recovered and analyzed.

FIG. 6 shows one detection system that includes a plurality of sources 200. A plurality of sources 200 may be deployed in the field in an area of interest. Each source 200 may be attached to an anchor device 602 that provides a connection between the source 200 and the ground 600. The anchor device 602 may be one of a spike or a tripod base, a dart base, or a weighted base. In one embodiment, the connection between the anchor device 602 and the source 200 may allow the source 200 to direct beams 202A, 204A, and 206A (and possibly 208A) in any direction rather than just vertically. In FIG. 6, the sources are directed vertically with respect to the ground 600. Once the plurality of sources 200 are deployed, they may begin to emit infrared radiation in the form of beams 202A, 204A, and 206A (and possibly 208A) skyward. An aerial vehicle 604 (e.g., a UAV, airplane, or helicopter) that includes detector 300 may fly over the area in which the plurality of sources are deployed and record a series of images. The rate at which controller 210 may switch between optical sources 202, 204, and 206 is limited by the capture rate of detector 300. That is the rate at which detector 300 can record images. In the case where detector 300 is a photosensor, detector 300 requires a certain amount of time between images to reset. Specifically, detector 300 needs sufficient time to generate accumulated voltages in the pixels, readout the accumulated voltages in the pixels, and reset the pixels to their default voltages all of which takes on the order of hundreds of microseconds. Assuming detector 300 requires 1 ms between images, detector 300 is still capable of recording 1,000 images a second. This means that controller 410 can cycle between optical sources 202, 204, and 206 at a rate of 1 kHz. If optical source 208 is provided, it is included in this cycle. By flying over an area in which the plurality of sources 200 are deployed, recording images based on infrared radiation emitted by the sources 200, and analyzing those images to determine the presence of a hazardous chemical, it is possible to determine in real time whether a hazardous chemical is present.

Figure 7:
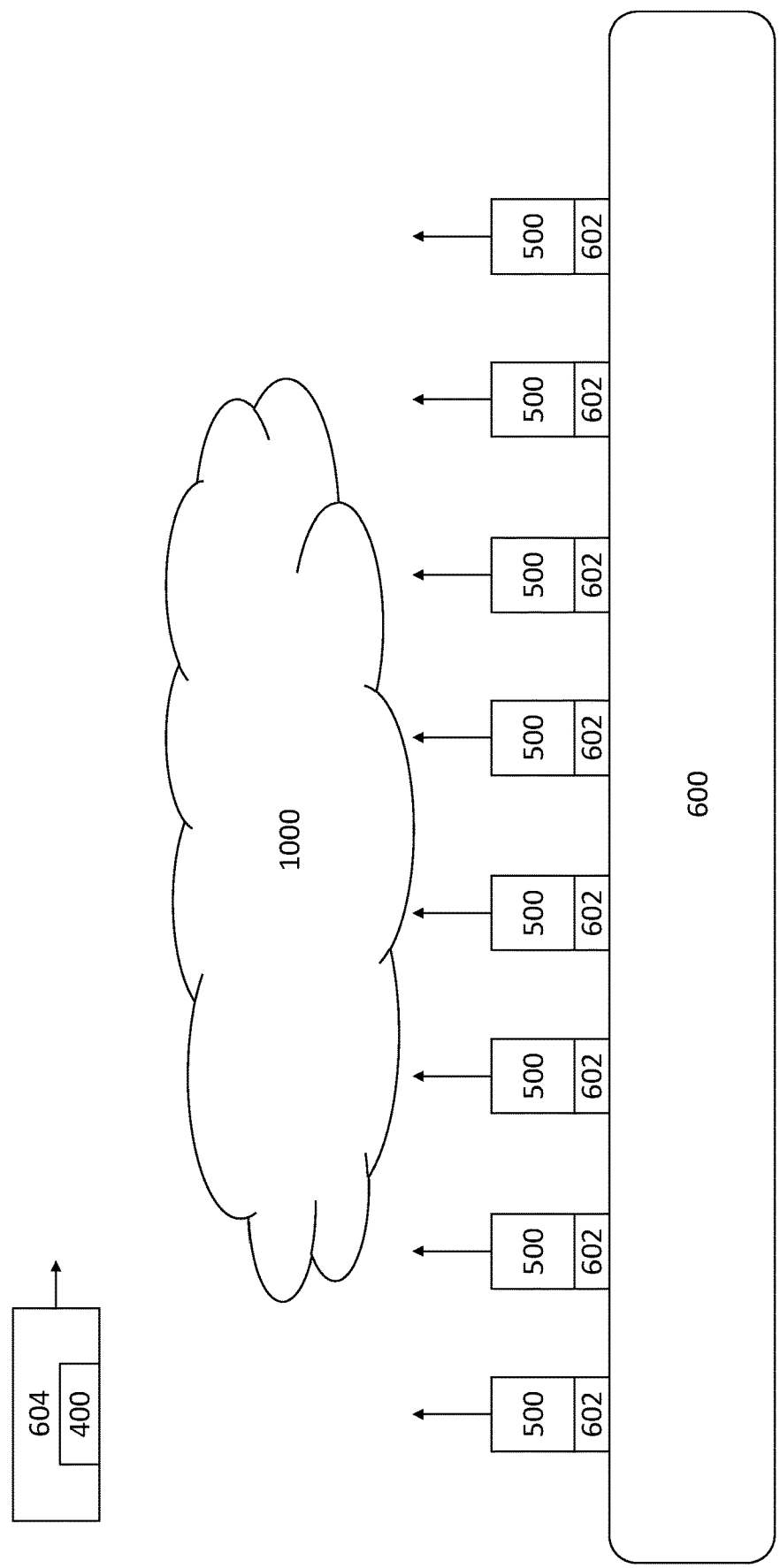
FIG. 7 is another illustration showing the deployment of retroreflectors in a field and the process by which data is recovered and analyzed.

FIG. 7 shows another detection system that employs a plurality of retroreflectors 500. FIG. 7 is substantially the same as FIG. 6, except that the plurality of sources 200 have been replaced with a plurality of retroreflectors 500 and source 300 has been replaced by source-detector 400. The optical sources 202, 204, and 206 (and possibly 208) within source-detector 400 emit beams of radiation 202A, 204A, and 206A (and possibly 208A) towards the retroreflectors 500 on the ground 600. In one embodiment, a beam steering mechanism may be placed in the optical path of beams 202A, 204A, and 206A (and possibly 208A) so as to raster beams 202A, 204A, and 206A (and possibly 208A) across the ground 600 such that they are incident on the plurality of retroreflectors 500. In another embodiment, detector 400 itself may be connected to a rastering mechanism that allows the entire detector 400 is pivot so as to sweep beams 202A, 204A, and 206A (and possibly 208A) across the retroreflectors. As discussed above, the plurality of retroreflectors 500 reflect radiation incident thereon back in the direction in which it was received. As described above, image sensor 302 may receive those reflected beams (either in attenuated or non-attenuated form) and generate data which is provided to controller 410. Controller 410 may then analyze the data from image sensor 302 to determine whether or not a hazardous chemical is disposed in the area over which the retroreflectors 500 are deployed, using the techniques discussed above.

In the exemplary embodiments described above, three optical sources are used to generate infrared beams. However, the invention is not limited to merely three optical sources. As one of ordinary skill will appreciate by providing additional optical sources a wider range of wavelength/frequencies may be covered by the optical sources. As the wavelength range increases, additional chemicals that may not have been significantly responsive to the wavelength range covered by three optical sources may now be detected. Moreover, additional optical sources add minimal time delays in generating and processing the resulting data. The power requirement of the additional optical sources may be mitigated by choosing relatively low power sources such an infrared light emitting diodes, among others.

In the exemplary embodiments described above, the images recorded by the image sensor 302 are used to produce stimulus value signals. However, those images may also be stored in memory. When a hazardous chemical is detected within the target detection area 1000, the corresponding IR images may be retrieved from memory and displayed on the notification device to provide the user with a visual indication of where the hazardous chemical is located. In another embodiment, IR images corresponding to non-hazardous chemicals may also be displayed on notification device to provide map of both hazardous and non-hazardous chemicals located in the field. The images may also be transmitted through the I/O connections to another device for further processing and/or display.

In the exemplary embodiments shown in FIGS. 6 and 7, an aerial vehicle 604 is used to move the detector 300 and source-detector 400 across the field, respectively. However, detector 300 and source-detector 400 may also be deployed on the ground 600 at a vantage that is sufficiently high above the ground 600 to provide a field-of-view that encompasses the entire area where sources 200 or retroreflectors 500 are deployed. Detector 300 and source-detector 400 may also be deployed on a tower or a vehicle that also provides a field-of-view that encompass the entire area where sources 200 or retroreflectors 500 are deployed. In such cases, the sources 200 and retroreflectors are not pointed vertically, but rather in the direction of the vantage point, tower, or vehicle. In yet another embodiment, the anchor device 602 may be replaced with buoy for deploying the sources 200 or retroreflectors over water.

While various example embodiments of the invention have been described above, it should be understood that they have been presented by way of example, and not limitation. It is apparent to persons skilled in the relevant art(s) that various changes in form and detail can be made therein. Thus, the disclosure should not be limited by any of the above described example embodiments, but should be defined only in accordance with the following claims and their equivalents.

In addition, it should be understood that the figures are presented for example purposes only. The architecture of the example embodiments presented herein is sufficiently flexible and configurable, such that it may be utilized and navigated in ways other than that shown in the accompanying figures.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

What is claimed is:
1. A standoff chemical detection system, comprising:
    a source that includes:
        a source controller,
        memory communicatively connected to the source controller,
        a plurality of optical sources each constructed to operate over different wavelength ranges and configured to receive instructions from the source controller, each optical source is constructed to emit a band of infrared radiation that at least partially overlaps with a band of infrared radiation generated by another optical source, and
        a power supply, wherein the source controller is configured to control the plurality of optical sources to emit respective infrared beams towards a target detection area in a sequential order; and a detector that includes:
an image sensor that includes a plurality of pixels,
a detector controller communicatively connected to the image sensor, and
memory communicatively connected to the detector controller,
wherein the image sensor is constructed to receive attenuated infrared beams emitted by the plurality of optical sources sequentially and at least partially attenuated by one or more chemicals in a target detection area,
wherein the image sensor is constructed to generate digital image data, corresponding to the plurality of pixels, based on the received attenuated infrared beams, and
wherein the detector controller is constructed to calculate stimulus value signals from the digital image data and determine whether a hazard chemical is located within the target detection area based on the calculated stimulus value signals.

2. The system of claim 1, wherein the plurality of optical sources are one of: lighting emitting diodes, quantum cascade lasers, interband cascade lasers, quantum dot emitters, or fluorescence emitters.

3. The system of claim 1, wherein the band of infrared radiation emitted by each optical source is within the mid-wave infrared region or the long wavelength infrared region.

4. The system of claim 1, wherein infrared beams emitted by the plurality of optical sources have a Gaussian or pseudo-Gaussian profile.

5. The system of claim 1, further comprising:
a reference optical source constructed to emit a band of radiation that does not overlap with the bands of radiation emitted the plurality of optical sources.

6. The system of claim 1, further comprising:
an optical element configured to collimate the infrared beams emitted by the plurality of optical sources.

7. The system of claim 1, wherein the image sensor is one of an infrared photodiode optical sensor, a PbSe image sensor, an Si microbolometer, a $VO_x$ microbolometer, an infrared focal plane array, or a deuterated triglycine sulfate detector.

8. The system of claim 1, further comprising:
a notification device constructed to display a name of the hazard chemical located within the target detection area and provide an audio alarm.

9. A source-detector for standoff chemical detection, comprising:
a source-detector controller;
memory communicatively connected to the source-detector controller;
a plurality of optical sources communicatively connected to the source-detector controller, wherein each of the plurality of optical sources is constructed to operate over different wavelengths and emit a band of infrared radiation that at least partially overlaps with a band of infrared radiation generated by another optical source;
a power supply; and
an image sensor that includes a plurality of pixels and is communicatively connected to the source-detector controller,
wherein the source-detector controller is configured to control the plurality of optical sources to emit respective infrared beams towards a target detection area in a sequential order,
wherein the image sensor is constructed to receive attenuated infrared beams emitted by the plurality of optical sources sequentially and at least partially attenuated by one or more chemicals in the target detection area,
wherein the image sensor is constructed to generate digital image data, corresponding to the plurality of pixels, based on the received attenuated infrared beams, and
wherein the source-detector controller is constructed to calculate stimulus value signals from the digital image data and determine whether a hazard chemical is located within the target detection area based on the calculated stimulus value signals.

10. The source-detector of claim 9, wherein the plurality of optical sources are one of: lighting emitting diodes, quantum cascade lasers, interband cascade lasers, quantum dot emitters, or fluorescence emitters.

11. The source-detector of claim 9, wherein the band of infrared radiation emitted by each optical source is within the mid-wave infrared region or the long wavelength infrared region.

12. The source-detector of claim 9, wherein the infrared beams emitted by the plurality of optical sources have a Gaussian or pseudo-Gaussian profile.

13. The source-detector of claim 9, further comprising:
a reference optical source constructed to emit a band of radiation that does not overlap with the bands of radiation emitted the plurality of optical sources.

14. The source-detector of claim 9, further comprising:
an optical element configured to collimate the infrared beams emitted by the plurality of optical sources.

15. The source-detector of claim 9, wherein the image sensor is one of an infrared photodiode optical sensor, a PbSe image sensor, an Si microbolometer, a $VO_x$ microbolometer, an infrared focal plane array, or a deuterated triglycine sulfate detector.

16. The source-detector of claim 9, further comprising:
a notification device constructed to display a name of the hazard chemical located within the target detection area and provide an audio alarm.

17. A source-detector for standoff chemical detection, comprising:
a source-detector controller;
memory communicatively connected to the source-detector controller;
a plurality of optical sources communicatively connected to the source-detector controller,
wherein the plurality of optical sources are constructed to emit a plurality of infrared beams over a plurality of different wavelength ranges, respectively, and
wherein the plurality of wavelength ranges at least partially overlap;
a power supply; and
an image sensor that includes a plurality of pixels and is communicatively connected to the source-detector controller,
wherein the source-detector controller is configured to control the plurality of optical sources to emit the plurality of infrared beams towards a target detection area in a sequential order,
wherein the image sensor is constructed to:
(i) receive a plurality of attenuated infrared beams that are formed by the attenuation of the plurality of infrared beams sequentially emitted by the plurality of optical sources due to one or more chemicals in the target detection area, (ii) generate digital image data, corresponding to the plurality of pixels, based on the received plurality of attenuated infrared beams, and (iii) provide the digital image data to the source-detector controller, and wherein the source-detector controller is constructed to calculate stimulus value signals from the digital image data and determine whether a hazard chemical is located within the target detection area based on the calculated stimulus value signals.

18. The source-detector of claim 17, wherein the plurality of infrared beams emitted by the plurality of optical sources have a Gaussian or pseudo-Gaussian profile.

19. The source-detector of claim 17, further comprising:
a reference optical source constructed to emit a beam with a wavelength range that does not overlap with the plurality of wavelength ranges.

20. The source-detector of claim 17, further comprising:
a notification device constructed to display a name of the hazard chemical located within the target detection area and provide an audio alarm.

* * * * *